(12) United States Patent
Wu et al.

(10) Patent No.: US 8,945,425 B2
(45) Date of Patent: Feb. 3, 2015

(54) SEMICONDUCTOR COMPOSITION

(75) Inventors: Yiliang Wu, Oakville (CA); Sandra J. Gardner, Oakville (CA); Anthony J. Wigglesworth, Oakville (CA); Ping Liu, Mississauga (CA); Nan-Xing Hu, Oakville (CA)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 818 days.

(21) Appl. No.: 13/088,476

(22) Filed: Apr. 18, 2011

(65) Prior Publication Data

US 2012/0261648 A1    Oct. 18, 2012

(51) Int. Cl.
*H01B 1/00*      (2006.01)
*H01L 29/08*     (2006.01)
*H01L 51/00*     (2006.01)
*C07D 495/04*    (2006.01)
*H01L 51/05*     (2006.01)

(52) U.S. Cl.
CPC .......... *H01L 51/0074* (2013.01); *C07D 495/04* (2013.01); *H01L 51/0558* (2013.01)

USPC ...................... 252/500; 257/40; 257/E51.024

(58) Field of Classification Search
None
See application file for complete search history.

(56) References Cited

U.S. PATENT DOCUMENTS 8,283,660 B2 * 10/2012 Wigglesworth et al. ........ 257/40

FOREIGN PATENT DOCUMENTS

JP          2009283786 A    * 12/2009

* cited by examiner

*Primary Examiner* — Harold Pyon
*Assistant Examiner* — Jaison Thomas
(74) *Attorney, Agent, or Firm* — Harness, Dickey & Pierce, P.L.C.

(57) ABSTRACT

An electronic device, such as a thin-film transistor, includes a semiconducting layer formed from a semiconductor composition. The semiconductor composition comprises a polymer binder and a small molecule semiconductor. The small molecule semiconductor in the semiconducting layer has a crystallite size of less than 100 nanometers. Devices formed from the composition exhibit high mobility and excellent stability.

17 Claims, 6 Drawing Sheets

SEMICONDUCTOR COMPOSITION

BACKGROUND

The present disclosure relates to thin-film transistors (TFTs) and/or other electronic devices comprising a semiconducting layer. The semiconducting layer is formed from a semiconductor composition as described herein. When the composition is used in the semiconducting layer of a device, high mobility and excellent stability may be achieved.

TFTs are generally composed of, on a substrate, an electrically conductive gate electrode, source and drain electrodes, an electrically insulating gate dielectric layer which separate the gate electrode from the source and drain electrodes, and a semiconducting layer which is in contact with the gate dielectric layer and bridges the source and drain electrodes. Their performance can be determined by the field effect mobility and the current on/off ratio of the overall transistor. High mobility and high on/off ratio are desired.

Organic thin-film transistors (OTFTs) can be used in applications such as radio frequency identification (RFID) tags and backplane switching circuits for displays, such as signage, readers, and liquid crystal displays, where high switching speeds and/or high density are not essential. They also have attractive mechanical properties such as being physically compact, lightweight, and flexible.

Organic thin-film transistors can be fabricated using low-cost solution-based patterning and deposition techniques, such as spin coating, solution casting, dip coating, stencil/screen printing, flexography, gravure, offset printing, ink jet-printing, micro-contact printing, and the like. To enable the use of these solution-based processes in fabricating thin-film transistor circuits, solution processable materials are therefore required. However, organic or polymeric semiconductors formed by solution processing tend to suffer from limited solubility, air sensitivity, and especially low field-effect mobility.

It would be desirable to develop a semiconducting composition that exhibits high field effect mobility, good film-forming properties, and proper morphology for high performance in a composite system.

BRIEF DESCRIPTION

The present application discloses, in various embodiments, electronic devices, semiconductor compositions used to make semiconducting layers in the electronic devices, and processes for making such electronic devices. The semiconducting layer is formed from a semiconductor composition that comprises a polymer binder and a crystalline small molecule semiconductor. The small molecule semiconductor has an average crystal size of less than about 50 nanometers. The resulting semiconducting layer achieves high mobility and has excellent stability. The electronic device comprises a semiconducting layer formed from such a semiconductor composition. In specific embodiments, the electronic devices are thin-film transistors.

Disclosed in embodiments is an electronic device including a semiconducting layer. The semiconducting layer comprises a polymer binder and a crystalline small molecule semiconductor. The small molecule semiconductor has an average crystal size that is at least two times smaller than the average crystal size of the small molecule semiconductor after the semiconducting layer has been thermally treated at a temperature that is greater than the melting temperature of the small molecule semiconductor. This aspect is explained in further detail herein. The resulting semiconducting layer has a field-effect mobility of at least 0.2 cm$^2$/V·sec, and may have a mobility of at least 0.4 cm$^2$/V·sec or at least 0.7 cm$^2$/V·sec.

The small molecule semiconductor may have an average crystal size of 100 nanometers or less, 50 nanometers or less, or 35 nanometers or less. The average crystal size of the small molecule semiconductor may be at least 5 nanometers.

The small molecule semiconductor may have the structure of Formula (I):

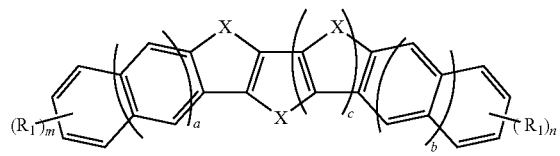

Formula (I)

wherein each $R_1$ is independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; m and n are the number of $R_1$ sidechains on their respective phenyl or naphthyl ring, and are independently an integer from 0 to 6; X is selected from the group consisting of O, S, and Se; and a, b, and c are independently 0 or 1.

The small molecule semiconductor may also have the structure of Formula (II):

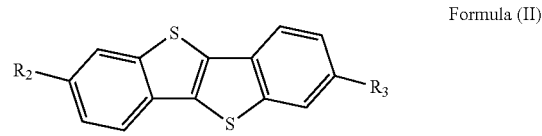

Formula (II)

wherein $R_2$ and $R_3$ are independently alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, or halogen.

The polymer binder may be a styrene-based polymer or an arylamine-based polymer. In embodiments, the polymer binder is a homopolymer. The polymer binder may be selected from polystyrene, poly(α-methyl styrene), poly(4-methyl styrene), poly(alpha-methyl styrene-co-vinyl toluene), poly(styrene-block-butadiene-block-styrene), poly(styrene-block-isopene-block-styrene), poly(vinyl toluene), a terpene resin, poly(styrene-co-2,4-dimethylstyrene), poly(chlorostyrene), polystyrene-co-α-methyl styrene), poly(styrene-co-butadiene), polycarbazole, a polytriarylamine, or poly(N-vinylcarbazole).

In particular embodiments, the polymer binder is a polystyrene polymer having a weight average molecular weight of from about 40,000 to about 2,000,000.

$R_2$ and $R_3$ may be independently $C_4$-$C_{16}$ alkyl.

The small molecule semiconductor may also have the structure of Formula (III):

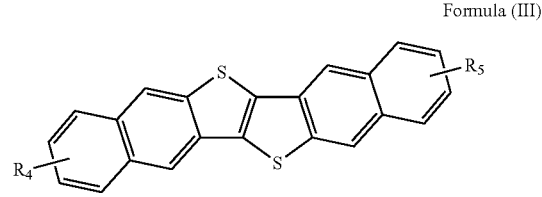

Formula (III)

wherein R₄ and R₅ are independently alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, and halogen.

The small molecule semiconductor may have the structure of Formula (IV):

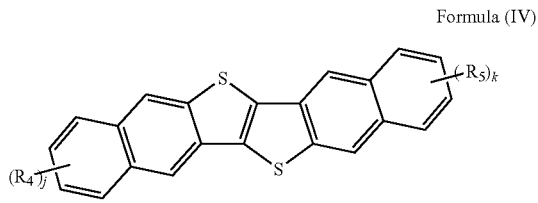

Formula (IV)

wherein R₄ and R₅ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; and j and k are independently an integer from 0 to 6.

In specific embodiments of Formula (IV), R₄ and R₅ are independently alkyl, j is 1, and k is 1.

The polymer binder may be a styrene-based polymer or an arylamine-based polymer.

The small molecule semiconductor may also have the structure of Formula (V):

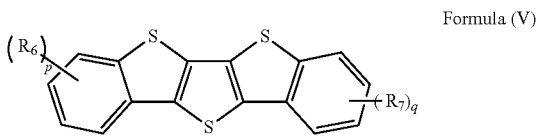

Formula (V)

wherein R₆ and R₇ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; and p and q are independently an integer from 0 to 4.

The small molecule semiconductor may also have the structure of Formula (VI):

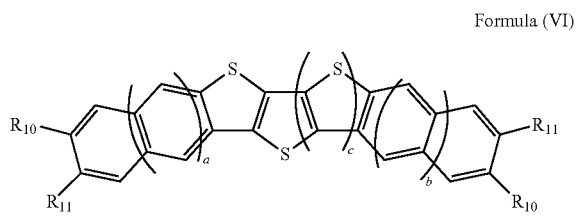

Formula (VI)

wherein R₁₀ and R₁₁ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; and a, b, and c are independently 0 or 1.

Also disclosed in embodiments is an electronic device comprising a semiconducting layer, the semiconducting layer comprising an amorphous polymer binder and a crystalline small molecule semiconductor. An x-ray diffraction pattern of the semiconductor layer has a primary diffraction peak with a Full Width at Half Maximum (FWHM) that is at least two times greater than a FWHM of the semiconducting layer after the semiconducting layer has been thermally treated at a temperature that is greater than the melting temperature of the small molecule semiconductor. Again, this aspect is further discussed herein. The resulting semiconducting layer has a field-effect mobility of at least 0.2 cm²/V·sec.

In specific embodiments, the x-ray diffraction pattern of the semiconductor layer has a primary diffraction peak with a FWHM of 0.20 degrees 2θ or greater.

Also disclosed in embodiments is a process for making a semiconducting layer of an electronic device. The process comprises spin-coating upon a surface a composition comprising a polymer binder and a small molecule semiconductor. The composition is spin-coated at a speed greater than about 2,000 RPMs. The composition may be spin-coated at a speed greater than about 2,500 RPMs, about 3,000 RPMs, or about 3,500 RPMs.

In embodiments, the small molecule semiconductor has the structure of Formula (I):

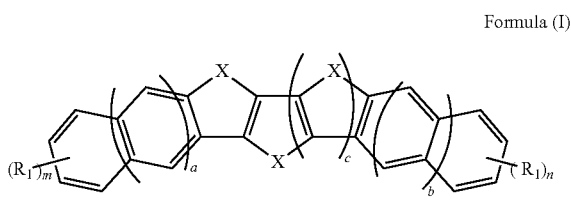

Formula (I)

wherein each R₁ is independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; m and n are the number of R₁ sidechains on their respective phenyl or naphthyl ring, and are independently an integer from 0 to 6; X is selected from the group consisting of O, S, and Se; and a, b, and c are independently 0 or 1.

In embodiments, the composition is not thermally treated after spin-coating.

Also disclosed in other embodiments is an electronic device comprising a semiconducting layer. The semiconducting layer comprises an amorphous polymer binder; and a small molecule semiconductor having the structure of Formula (I):

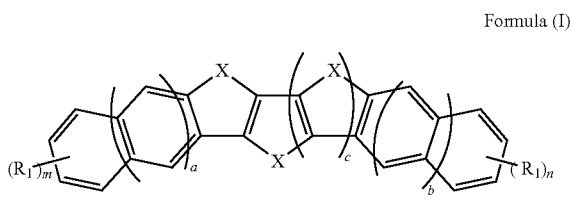

Formula (I)

wherein each R₁ is independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; m and n are the number of R₁ sidechains on their respective phenyl or naphthyl ring, and are independently an integer from 0 to 6; X is selected from the group consisting of O, S, and Se; and a, b, and c are independently 0 or 1. The small molecule semiconductor has an average crystal size of 100 nanometers or less in the semiconductor layer.

In specific embodiments, the amorphous polymer binder is a styrene-based polymer, and the small molecule semiconductor has the structure of Formula (II):

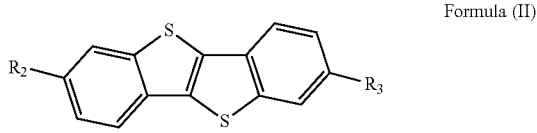

Formula (II)

wherein $R_2$, and $R_3$ are independently alkyl or substituted alkyl. The small molecule semiconductor has an average crystal size of 50 nm or less in the semiconductor layer.

These and other non-limiting characteristics of the disclosure are more particularly disclosed below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following is a brief description of the drawings, which are presented for the purposes of illustrating the exemplary embodiments disclosed herein and not for the purposes of limiting the same.

DETAILED DESCRIPTION

Figure 1:
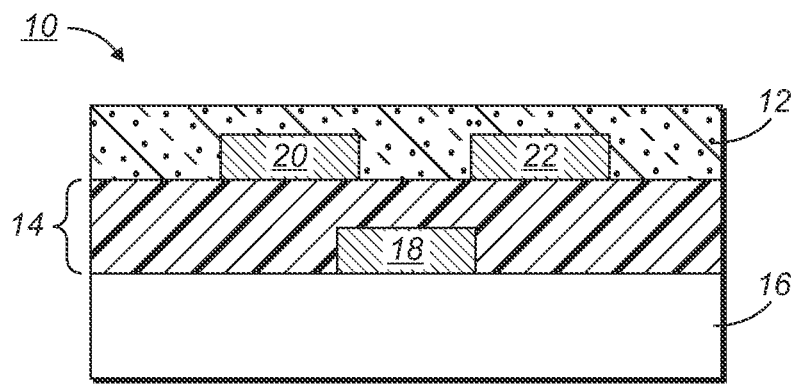
FIG. 1 is a diagram of a first embodiment of a TFT according to the present disclosure.

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range of "from about 2 to about 10" also discloses the range "from 2 to 10."

The term "comprising" is used herein as requiring the presence of the named component and allowing the presence of other components. The term "comprising" should be construed to include the term "consisting of", which allows the presence of only the named component, along with any impurities that might result from the manufacture of the named component.

The present disclosure relates to a composition comprising an amorphous polymer binder and a crystalline small molecule semiconductor as described further herein. A semiconducting layer formed from the composition is very stable in air and has high mobility compared to a semiconducting layer formed from only the small molecule semiconductor itself. These semiconductor compositions are useful for forming layers in electronic devices, such as thin film transistors (TFTs). The semiconducting layer of the present disclosure has a unique feature—the crystalline small molecule semiconductor in the semiconducting layer has a depressed crystal size.

It should be noted that the characteristic of depressed crystal size can be achieved through various means, for example, by drying off solvents at a high speed to reduce the time for crystallization, by avoiding the use of high process temperatures (e.g. during drying or annealing) to avoid the growth of large crystals, by optionally adding a crystallization inhibitor component, etc. However, no matter what process is used, it has been found that the semiconducting layer will offer a high performance (e.g. high charge carrier mobility) as long as the small molecule semiconductor in the final semiconducting layer has a depressed crystal size. It is generally believed that a semiconducting layer with a large crystal size is preferred for high performance. In contrast, we disclose here that a semiconducting layer with a smaller crystal size is preferred for high performance. The term "depressed crystal size" is comparative. Since the crystal size of the small molecule semiconductor in the semiconducting layer depends on the processing method, to have a consistent comparison, the crystal size of the small molecule semiconductor in the same semiconducting layer after a thermal treatment at a temperature above the melting point of the small molecule semiconductor is used as the basis for comparison, because thermal treatment (such as annealing) usually results in crystals of similar size regardless of the methods used before annealing and therefore provides a consistent basis for comparison between processing methods.

In embodiments, this is evidenced by the small molecule semiconductor having an average crystal size that is at least two times smaller than that of the small molecule semiconductor in the same semiconducting layer after thermal treatment at a temperature above the melting point of the small molecule semiconductor. Put another way, when the average crystal size of the small molecule semiconductor in the semiconducting layer of the present disclosure is compared to the average crystal size of the small molecule semiconductor in a semiconducting layer that is of the same composition and has been processed in the same way but with the addition of a thermal treatment, the average crystal size in the non-thermally treated layer is at least half the average crystal size in the thermally treated layer. In some embodiments, the small molecule semiconductor in the semiconducting layer has an average crystal size of 100 nanometers or less, including 50 nanometers or less.

This depressed crystal size is also evidenced in an x-ray diffraction (XRD) pattern of a semiconducting layer or film containing the crystalline small molecule semiconductor. An X-ray diffraction pattern of the semiconducting layer of the present disclosure has a primary diffraction peak with a Full Width at Half Maximum (FWHM) that is at least two times greater than a FWHM of the semiconducting layer after the semiconducting layer has been thermally treated at a temperature that is greater than the melting temperature of the small molecule semiconductor. Put another way, when the XRD pattern of the semiconducting layer of the present disclosure is compared to the XRD pattern of a semiconducting layer that has the same composition and has been processed in the same way but with the addition of a thermal treatment, the primary diffraction peak in the non-thermally treated layer will have a FWHM that is at least twice the FWHM of the primary diffraction peak in the thermally treated layer. The term "primary diffraction peak" refers to the diffraction peak on the XRD pattern having the lowest diffraction angle (2θ), or in other words the first main peak. An XRD pattern is a graph of intensity versus scattering angle (2θ), and the location of the primary diffraction peak is generally at the same scattering angle for both the non-thermally treated layer and the thermally treated layer, or only slightly different. The intensity does not need to be normalized, as this will not change the FWHM of the primary diffraction peak. In some embodiments, the primary diffraction peak has a FWHM of 0.20 degrees 2θ or greater, including 0.25 degrees or greater. One of ordinary skill in the art is able to distinguish between diffraction peaks and small peaks that may be present in the baseline or background.

FIG. 1 illustrates a bottom-gate bottom-contact TFT configuration according to the present disclosure. The TFT 10 comprises a substrate 16 in contact with the gate electrode 18 and a gate dielectric layer 14. The gate electrode 18 is depicted here atop the substrate 16, but the gate electrode could also be located in a depression within the substrate. It is important that the gate dielectric layer 14 separates the gate electrode 18 from the source electrode 20, drain electrode 22, and the semiconducting layer 12. The semiconducting layer 12 runs over and between the source and drain electrodes 20 and 22. The semiconductor has a channel length between the source and drain electrodes 20 and 22.

Figure 2:
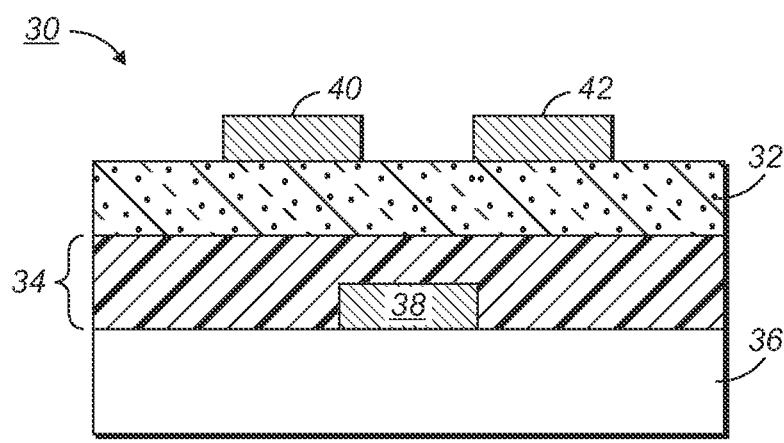
FIG. 2 is a diagram of a second embodiment of a TFT according to the present disclosure.

FIG. 2 illustrates another bottom-gate top-contact TFT configuration according to the present disclosure. The TFT 30 comprises a substrate 36 in contact with the gate electrode 38 and a gate dielectric layer 34. The semiconducting layer 32 is placed on top of the gate dielectric layer 34 and separates it from the source and drain electrodes 40 and 42.

Figure 3:
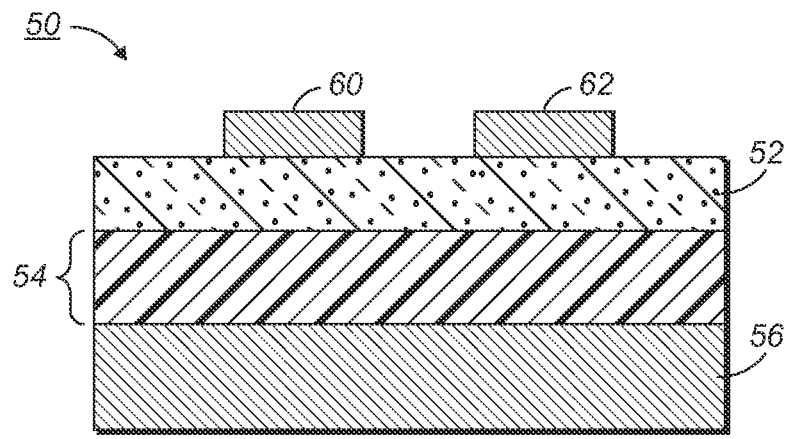
FIG. 3 is a diagram of a third embodiment of a TFT according to the present disclosure.

FIG. 3 illustrates a bottom-gate bottom-contact TFT configuration according to the present disclosure. The TFT 50 comprises a substrate 56 which also acts as the gate electrode and is in contact with a gate dielectric layer 54. The source electrode 60, drain electrode 62, and semiconducting layer 52 are located atop the gate dielectric layer 54.

Figure 4:
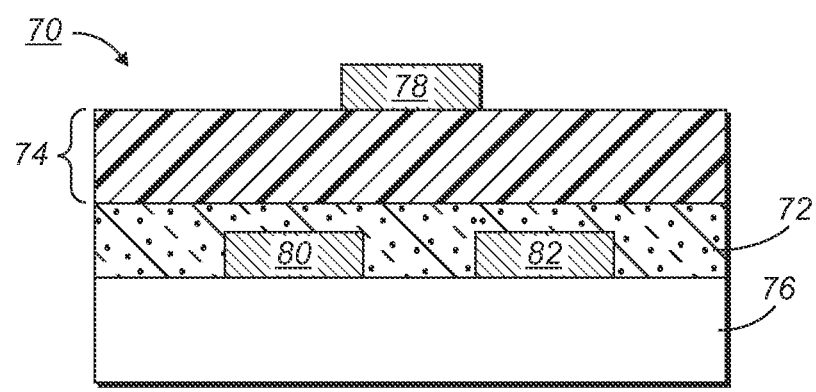
FIG. 4 is a diagram of a fourth embodiment of a TFT according to the present disclosure.

FIG. 4 illustrates a top-gate top-contact TFT configuration according to the present disclosure. The TFT 70 comprises a substrate 76 in contact with the source electrode 80, drain electrode 82, and the semiconducting layer 72. The semiconducting layer 72 runs over and between the source and drain electrodes 80 and 82. The gate dielectric layer 74 is on top of the semiconducting layer 72. The gate electrode 78 is on top of the gate dielectric layer 74 and does not contact the semiconducting layer 72.

The semiconductor composition comprises a polymer binder and a small molecule semiconductor. In embodiments, the small molecule semiconductor may have the structure of Formula (I):

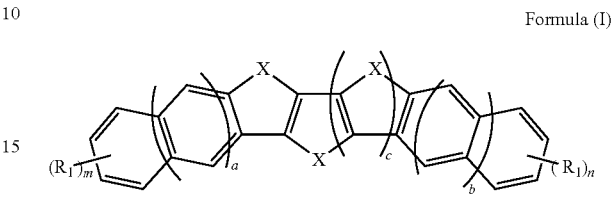

Formula (I)

wherein each $R_1$ is independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano (CN), and halogen; m and n are the number of $R_1$ sidechains on their respective phenyl or naphthyl ring, and are independently an integer from 0 to 6; X is selected from the group consisting of O, S, and Se; and a, b, and c are independently 0 or 1. In this regard, when a or b is 0, the exterior portion of the compound will be a phenyl ring that may have up to 4 sidechains. When a or b is 1, the exterior portion of the compound will be a naphthyl ring that may have up to 6 sidechains.

The term "alkyl" refers to a radical composed entirely of carbon atoms and hydrogen atoms which is fully saturated and of the formula —$C_nH_{2n+1}$. The alkyl radical may be linear, branched, or cyclic.

The term "alkenyl" refers to a radical composed entirely of carbon atoms and hydrogen atoms which contains at least one carbon-carbon double bond.

The term "alkynyl" refers to a radical composed entirely of carbon atoms and hydrogen atoms which contains at least one carbon-carbon triple bond.

The term "aryl" refers to an aromatic radical composed entirely of carbon atoms and hydrogen atoms. When aryl is described in connection with a numerical range of carbon atoms, it should not be construed as including substituted aromatic radicals. For example, the phrase "aryl containing from 6 to 10 carbon atoms" should be construed as referring to a phenyl group (6 carbon atoms) or a naphthyl group (10 carbon atoms) only, and should not be construed as including a methylphenyl group (7 carbon atoms).

The term "heteroaryl" refers to an aromatic radical composed of carbon atoms, hydrogen atoms, and one or more heteroatoms. The carbon atoms and the heteroatoms are present in a cyclic ring or backbone of the radical. The heteroatoms are selected from O, S, and N. Exemplary heteroaryl radicals include thienyl and pyridinyl.

The term "alkoxy" refers to an alkyl radical which is attached to an oxygen atom, i.e. —O—$C_nH_{2n+1}$.

The term "alkylthio" refers to an alkyl radical which is attached to a sulfur atom, i.e. —S—$C_nH_{2n+1}$.

The term "trialkylsilyl" refers to a radical composed of a tetravalent silicon atom having three alkyl radicals attached to the silicon atom, i.e. —Si(R)$_3$. The three alkyl radicals may be the same or different.

The term "substituted" refers to at least one hydrogen atom on the named radical being substituted with another functional group, such as halogen, —CN, —NO$_2$, —COOH, and —SO$_3$H. An exemplary substituted alkyl group is a perhaloalkyl group, wherein one or more hydrogen atoms in an alkyl group are replaced with halogen atoms, such as fluorine, chlorine, iodine, and bromine. Besides the aforementioned functional groups, an aryl or heteroaryl group may also be substituted with alkyl or alkoxy. Exemplary substituted aryl groups include methylphenyl and methoxyphenyl. Exemplary substituted heteroaryl groups include dodecylthienyl.

Generally, the alkyl and alkoxy groups each independently contain from 1 to 30 carbon atoms. Similarly, the aryl groups independently contain from 6 to 30 carbon atoms.

When a, b, and c are 0, X is sulfur, and m and n are each 1, the molecule of Formula (I) is also formally known as a disubstituted-[1]benzothieno[3,2-b]benzothiophene. The [1]benzothieno[3,2-b]benzothiophene moiety (when m and n are each 0) may be abbreviated herein as "BTBT". For example, the semiconductor of Formula (I) could be referred to as a disubstituted-BTBT.

In embodiments, the small molecule semiconductor has a band gap of from about 1.5 to about 3.5 eV, including from about 1.8 to about 2.8 eV. This large band gap typically means that the small molecule semiconductor has better stability in air, when compared to a pentacene-based semiconductor. The small molecule semiconductor has a crystalline or liquid crystalline structure. In specific embodiments, the semiconductor of Formula (I) is colorless in the visible region of the electromagnetic spectrum (i.e. from 390 nm to 750 nm). Colorless semiconductors not only provide excellent stability due to their large band gaps, but also offer advantage in transparency for transparent device applications.

Five particular variations of the compound of Formula (I) are contemplated by the present disclosure. In one variation, the small molecule semiconductor has the structure of Formula (II):

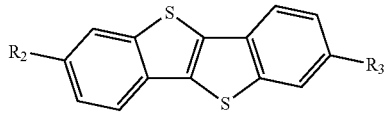

Formula (II)

wherein $R_2$ and $R_3$ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen. On this semiconductor compound of Formula (II), $R_2$ is located at the 2-position and $R_3$ is located at the 7-position. Thus, the compound of Formula (II) could be referred to as a 2,7-disubstituted-BTBT. Referring to Formula (I), the compound of Formula (II) is obtained when a, b, and c are 0.

In some embodiments, the $R_2$ and $R_3$ are independently selected from alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen. In some other embodiments, $R_2$ and $R_3$ are independently selected from alkyl and substituted alkyl, and the small molecule semiconductor is combined with specific polymer binders to achieve high field-effect mobility. The polymer binders will be explained further herein. The alkyl group may contain from about 4 to about 30 carbon atoms, including from about 4 to about 16 carbon atoms. Exemplary alkyl groups include butyl, pentyl, hexyl, heptyl, octyl, decyl, dodecyl, tridecyl, hexadecyl, and the like. In some embodiments, the alkyl group has an odd number of carbon atoms; in other embodiments the alkyl group has an even number of carbon atoms. In particular embodiments, $R_2$ and $R_3$ are the same.

In another variation, the small molecule semiconductor has the structure of Formula (III):

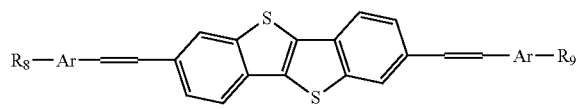

Formula (III)

wherein $R_8$, and $R_9$ are independently alkyl or substituted alkyl; and each Ar is independently an arylene or heteroarylene group. Referring again to Formula (I), the compound of Formula (III) is obtained when a, b, and c are 0; m and n are 1; and each $R_1$ is alkenyl or substituted alkenyl. The alkyl group may contain from 1 to about 30 carbon atoms, including from about 4 to about 18 carbon atoms.

The term "arylene" refers to an aromatic radical composed entirely of carbon atoms and hydrogen atoms that can form single bonds with two different atoms. An exemplary arylene group is phenylene ($-C_6H_4-$).

The term "heteroarylene" refers to an aromatic radical composed of carbon atoms, hydrogen atoms, and one or more heteroatoms, and that can form single bonds with two different atoms. The carbon atoms and the heteroatoms are present in a cyclic ring or backbone of the radical. The heteroatoms are selected from O, S, and N. An exemplary heteroarylene group is 2,5-thienyl.

In a third variation, the small molecule semiconductor has the structure of Formula (IV):

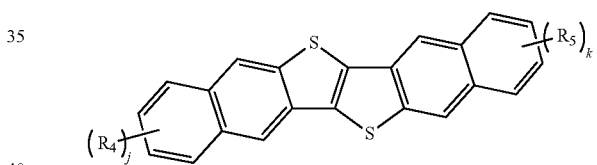

Formula (IV)

wherein $R_4$ and $R_5$ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; and j and k are independently an integer from 0 to 6. Referring again to Formula (I), the compound of Formula (IV) is obtained when a and b are both 1, and c is 0. The $R_4$ and $R_5$ sidechains may be located on any carbon atom of the exterior naphthyl portions of the compound of Formula (IV).

In specific embodiments of Formula (IV), $R_4$ and $R_5$ are independently alkyl, j is 1, and k is 1.

In the next variation, the small molecule semiconductor has the structure of Formula (V):

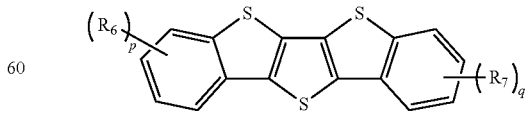

Formula (V)

wherein $R_6$ and $R_7$ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; and p and q are independently an integer from 0 to 4. Referring again to Formula (I), the compound of Formula (V) is obtained when a and b are both 0, and c is 1.

In the final variation, the small molecule semiconductor has the structure of Formula (VI):

Formula (VI)

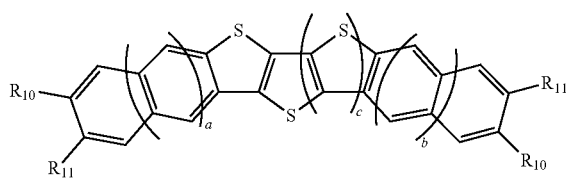

wherein $R_{10}$ and $R_{11}$ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; and a, b, and c are independently 0 or 1.

In particular embodiments of Formula (VI), $R_{10}$ is halogen or cyano, and $R_{11}$ is alkyl, substituted alkyl, alkenyl, substituted alkenyl, or ketonyl. In other embodiments, $R_{11}$ is halogen or cyano, and $R_{10}$ is alkyl, substituted alkyl, alkenyl, substituted alkenyl, or ketonyl.

Other specific variations on the small molecule semiconductor of Formula (I) are also shown here as Formulas (1)-(50):

Formula (1)

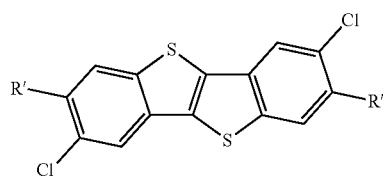

Formula (2)

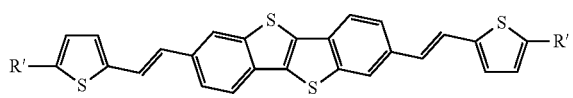

Formula (3)

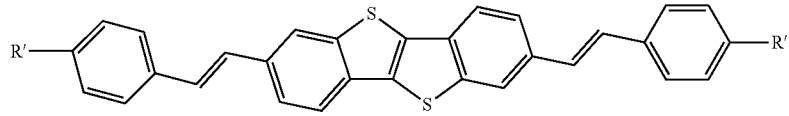

Formula (4)

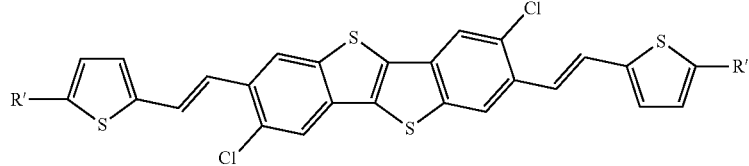

Formula (5)

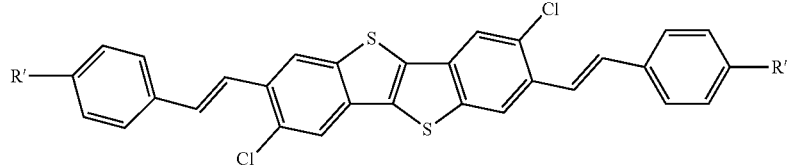

Formula (6)

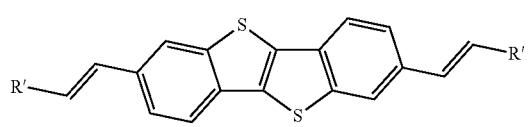

Formula (7)

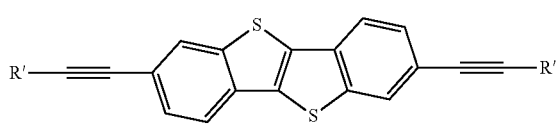

Formula (8)

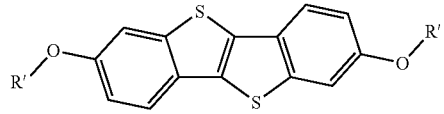

Formula (9)

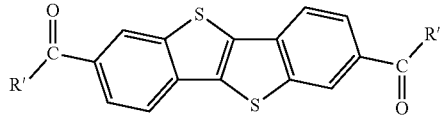

Formula (10)

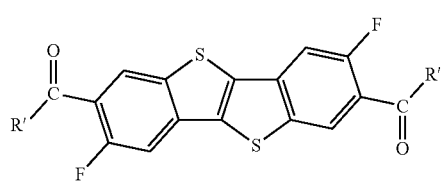

Formula (11)

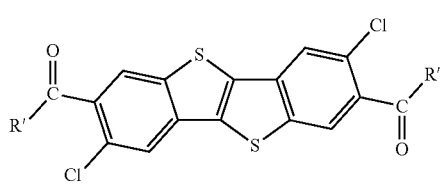

-continued
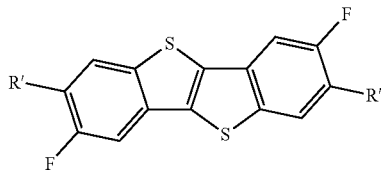
Formula (12)
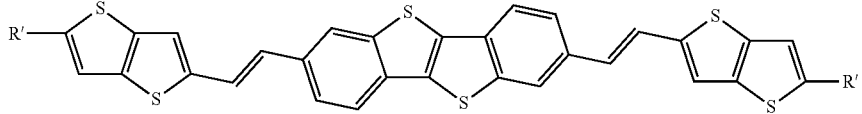
Formula (13)
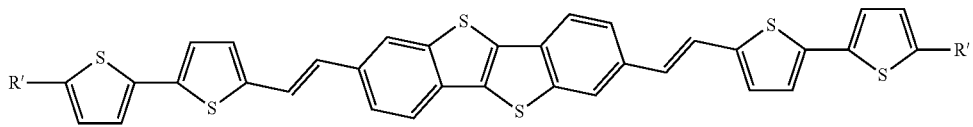
Formula (14)
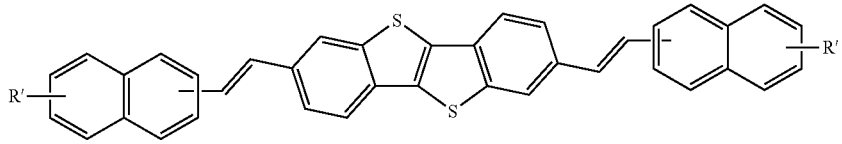
Formula (15)
Formula (16)
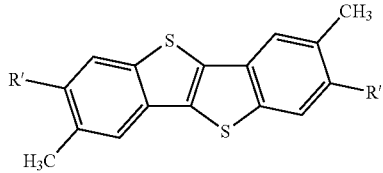
Formula (17)
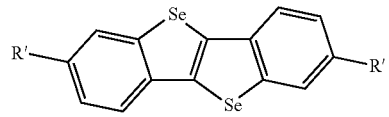
Formula (18)
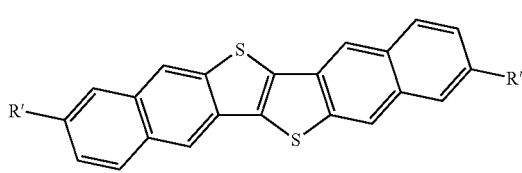
Formula (19)
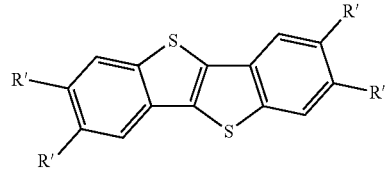
Formula (20)
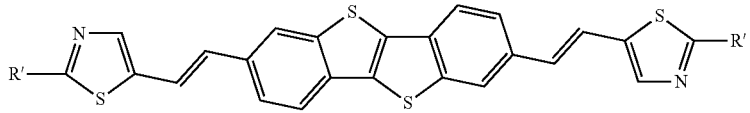
Formula (21)
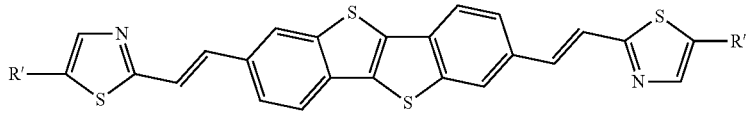
Formula (22)
Formula (23)
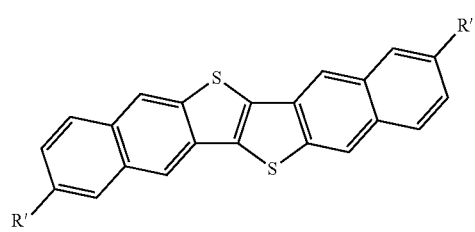

-continued
Formula (24)
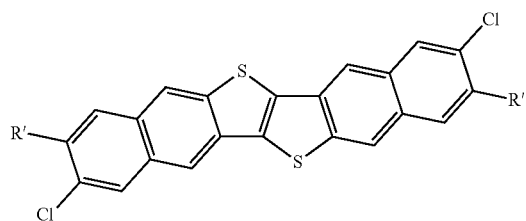
Formula (25)
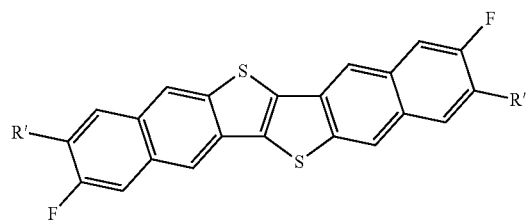
Formula (26)
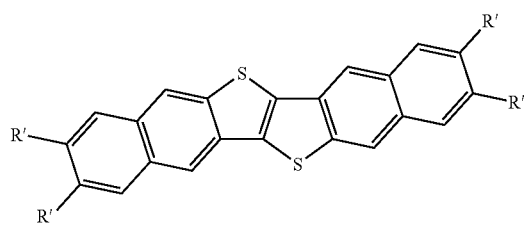
Formula (27)
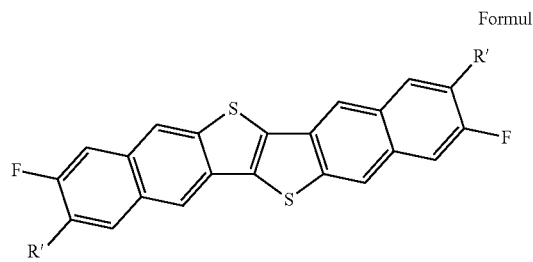
Formula (28)
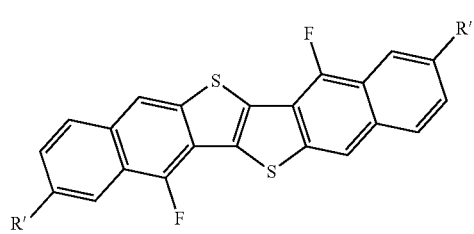
Formula (29)
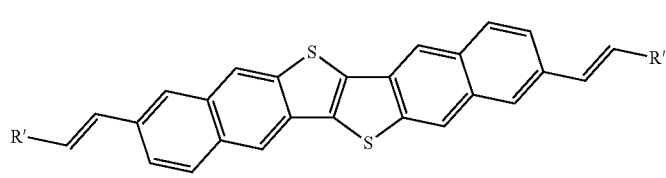
Formula (30)
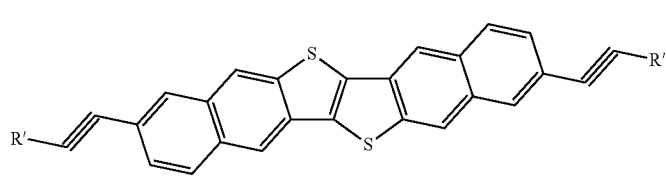
Formula (31)
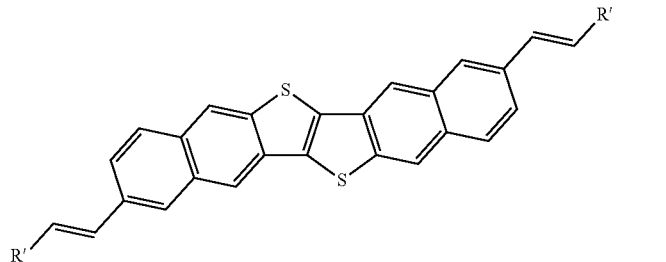
Formula (32)
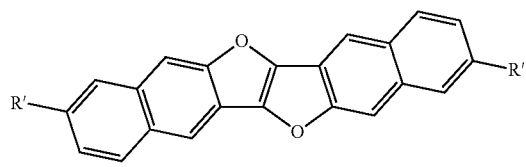
Formula (33)
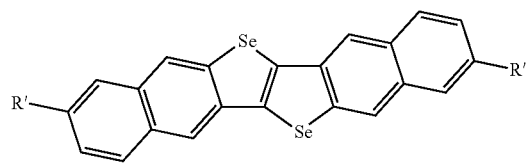

-continued

Formula (34)
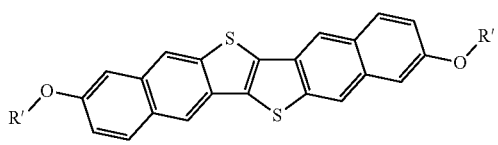

Formula (35)
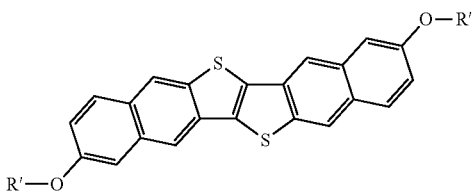

Formula (36)
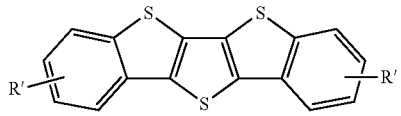

Formula (37)
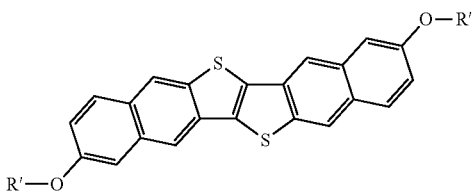

Formula (38)
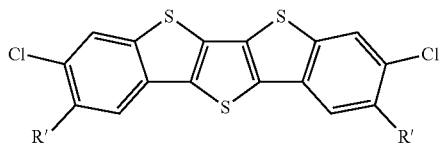

Formula (39)
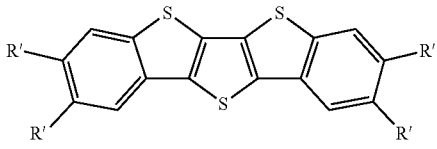

Formula (40)
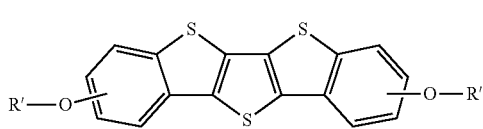

Formula (41)
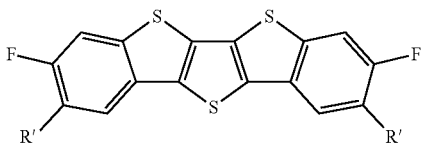

Formula (42)
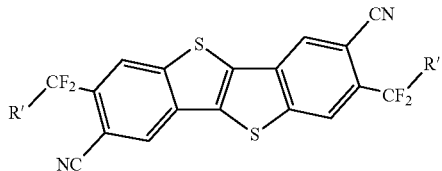

Formula (43)
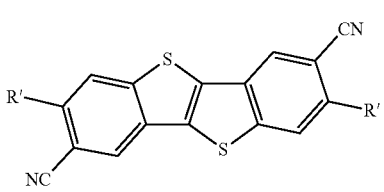

Formula (44)
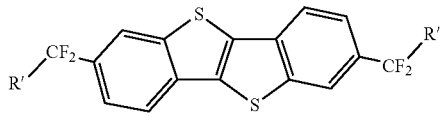

Formula (45)
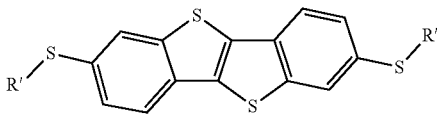

Formula (46)
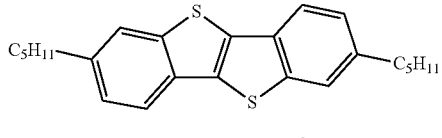

Formula (47)
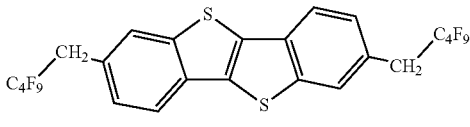

Formula (48)
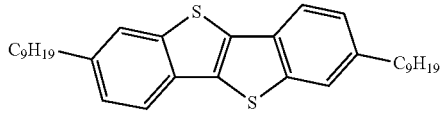

Formula (49)
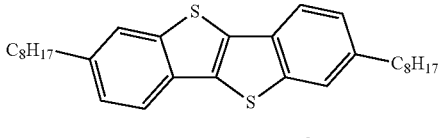

Formula (50)
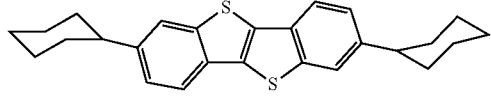

wherein each R' is independently alkyl or substituted alkyl containing from about 4 to about 20 carbon atoms, including from about 4 to about 16 carbon atoms.

The semiconducting compounds of Formulas (2), (3), (7), (8), (9), (13), (14), (15), (20), (21), and (43) through (50) are also exemplary compounds of Formula (II).

The semiconducting compounds of Formulas (2), (3), (13), (14), (15), (20), and (21) are also exemplary compounds of Formula (III).

The semiconducting compounds of Formulas (22), (23), (24), (25), (26), (27), (28), (29), (30), (31), (34), and (35) are also exemplary compounds of Formula (IV).

The semiconducting compounds of Formulas (36), (37), (38), (39), and (40) are also exemplary compounds of Formula (V).

The semiconducting compounds of Formulas (4), (5), (10), (11), (12), (18), (19), (24), (25), (26), (27), (37), (38), (39), (41), and (42) are also exemplary compounds of Formula (VI).

Various methods known in the arts can be used to make the small molecule semiconductors disclosed in this invention. For example, methods of producing the small molecule semiconductor of Formula (II) include reacting a 2,7-dihalo-BTBT A with an alkyne to form a 2,7-dialkyn-1-yl-BTBT 1. This initial reaction is illustrated below:

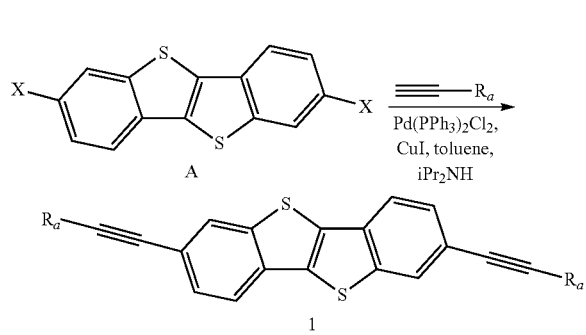

wherein X is a halogen, $R_a$ is alkyl, $Ph(PPh_3)_2Cl_2$ is bis(triphenylphosphine) palladium(II) chloride, CuI is copper iodide, and $iPr_2NH$ is diisopropylamine. As shown here, the two $R_a$ groups are identical. However, the two $R_a$ groups can be different as well, for example by using a blocking/protecting group on one of the X groups, performing a first reaction with a first alkyne to convert the unprotected X group, removing the blocking/protecting group, then subsequently performing a second reaction with a second different alkyne.

Next, the 2,7-dialkyn-1-yl-BTBT 1 can be reduced to a 2,7-dialkyl-[1]benzothieno[3,2-b]benzothiophene 1a as depicted below:

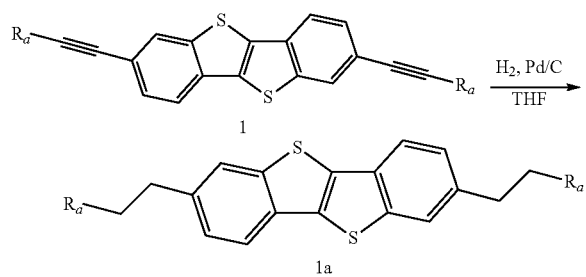

wherein Pd/C is a palladium on carbon catalyst and THF is tetrahydrofuran. Similar reactions can be performed for the other possible $R_a$ substituents.

Methods for preparing compounds 1a also includes the reaction of the [1]benzothieno[3,2-b]-benzothiophene core B with a substituted acid chloride in presence of aluminum trichloride to form a 2,7-diketonyl BTBT 2.

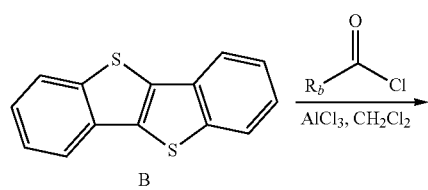

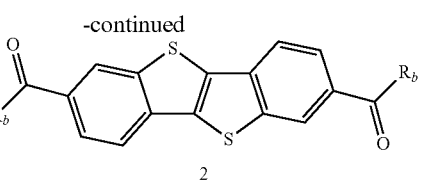

Next, the diketonyl BTBT 2 is deoxygenated using a modified Wolff-Kishner reduction using hydrazine in the presence of potassium hydroxide in diethylene glycol. This forms 2,7-dialkyl-[1]benzothieno[3,2-]benzothiophene 1b.

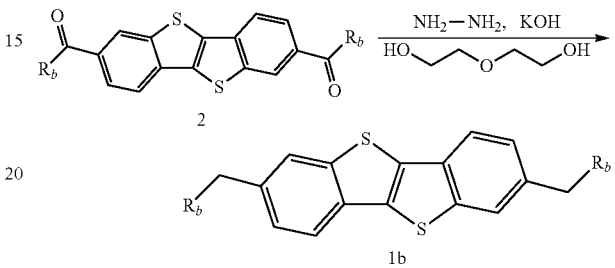

This 2-step method is particularly effective for short $R_b$ substituents ($C_2$-$C_8$).

The small molecule semiconductor by itself has poor film-forming properties, which is attributed to its crystalline or liquid crystalline nature. Thus, the semiconductor composition also comprises a polymer binder, which allows a uniform film to be achieved, significantly improving device performance. The polymer binder can be considered as forming a matrix within which the small molecule semiconductor is dispersed.

Any suitable polymer can be used as the polymer binder for the semiconductor composition. In some embodiments, the polymer is an amorphous polymer. The amorphous polymer may have a glass transition temperature less than the melting point temperature of the small molecule semiconductor. In other embodiments, the amorphous polymer has a glass transition temperature greater than the melting point temperature of the small molecule semiconductor. In embodiments, the polymer has a dielectric constant less than 4.5, preferably less than 3.5, including less than 3.0, as measured at 60 Hz at room temperature. In embodiments, the polymer is selected from polymers containing only C, H, F, Cl, or N atoms. In some embodiments, the polymer is a low polarity polymer, such as a hydrocarbon polymer or a fluorocarbon polymer without any polar groups. For example, polystyrene is an amorphous polymer and has a dielectric constant about 2.6. A list of other low polarity polymers includes but is not limited to the following: fluoropolyarylether, poly(p-xylylene), poly(vinyl toluene), poly(α-methyl styrene), poly(a-vinylnaphthalene), polyethylene, polypropylene, polyisoprene, poly(tetrafluoroethylene), poly(chlorotrifluoroethylene), poly(2-methyl-1,3-butadiene), poly(cyclohexyl methacrylate), poly(chlorostyrene), poly(4-methyl styrene), poly(vinyl cyclohexane), polyphenylene, poly-p-phenylvinylidenes, poly(arylene ether), polyisobutylene, poly(2,6-dimethyl-1,4-phenylene ether), poly[1,1-(2-methyl propane)bis-(4-phenyl)carbonate], poly(a-a-a'-a' tetrafluoro-p-xylylene), fluorinated polyimide, poly(ethylene/tetrafluoroethylene), poly(ethylene/chlorotrifluoroethylene), fluorinated ethylene/propylene copolymer, poly(styrene-co-a-methyl styrene), poly(styrene/butadiene), poly(styrene/2,4-dimethylstyrene), CYTOP, poly(propylene-co-1-butene), poly(styrene-co-vinyl toluene), polystyrene-block-butadiene-block-styrene), poly(styrene-block-isopene-block-styrene), terpene resin, poly(N-vinylcarbazole), polycarbazole, polytriarylamine, and the like.

It has been found that the mobility of the semiconducting layer formed by the semiconductor composition can be affected by the combination of small molecule semiconductor with certain polymers. The compounds of Formula (I) can be combined with many different polymers. In some particular embodiments, the polymer binder is a styrene-based polymer.

Styrene-based polymers contain a repeating unit derived from a styrene monomer of Formula (a):

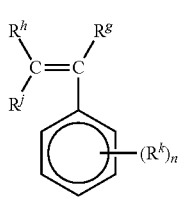

Formula (a)

wherein $R^g$, $R^h$, $R^j$, and $R^k$ are independently selected from hydrogen, halogen, and $C_1$-$C_{20}$ alkyl; and n is an integer from 0 to 5. The styrene monomer can be styrene ($R^g$, $R^h$, and $R^j$ are all hydrogen, n=0), alpha-methyl styrene ($R^g$ is methyl, $R^h$ and $R^j$ are hydrogen, n=0), or 4-methyl styrene ($R^g$, $R^h$, and $R^j$ are all hydrogen, n=1, $R^k$ is methyl in the 4-position). The term "styrene-based polymer" is intended to encompass both homopolymers and copolymers. The term "copolymer" is intended to encompass random, alternative, and block copolymers.

In other particular embodiments, the polymer binder is an arylamine-based polymer. An arylamine-based polymer has a repeating unit derived from a monomer having the structure of Formula (b), Formula (c) or Formula (d):

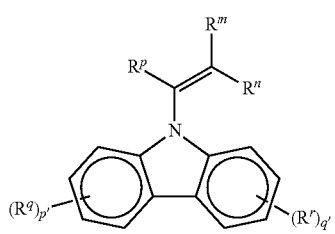

Formula (b)

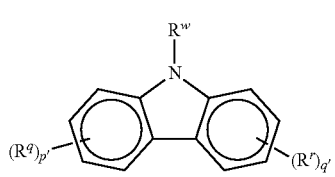

Formula (c)

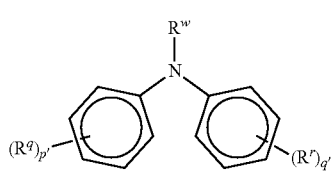

Formula (d)

wherein $R^m$, $R^n$, $R^p$, $R^q$, and $R^r$ are independently selected from hydrogen, halogen, $C_1$-$C_{20}$ alkyl, and aryl; p' and q' are independently an integer from 0 to 5; and $R^w$ is selected from $C_1$-$C_{20}$ alkyl, aryl, and substituted aryl. The term "arylamine-based" polymers is intended to encompass poly(N-vinyl carbazole), polycarbazole, and triarylamine-based polymers.

In specific embodiments, the styrene-based polymer and the arylamine-based polymer include polystyrene, poly(α-methyl styrene), poly(4-methyl styrene), poly(vinyl toluene), poly(α-methyl styrene-co-vinyl toluene), polystyrene-block-butadiene-block-styrene), poly(styrene-block-isopene-block-styrene), a terpene resin, poly(styrene-co-2,4-dimethylstyrene), poly(chlorostyrene), poly(styrene-co-α-methyl styrene), poly(styrene/butadiene), poly(N-vinylcarbazole), polycarbazole, and polytriarylamines. It should be noted that one or more polymer binders can be used in the semiconductor composition.

The compound of Formula (II) works best when combined with the polymer binders discussed above, particularly, the styrene-based polymer or the arylamine-based polymer described above.

In more specific embodiments, the polymer binder is a styrene-based polymer. In particular embodiments, the styrene-based polymer has a weight average molecular weight of from about 40,000 to about 2,000,000. In some embodiments, the styrene-based polymer has a molecular weight of from about 100,000 to about 1,000,000. In one preferred embodiment, the polymer binder is polystyrene, poly(alpha-methyl styrene), or poly(4-methyl styrene) having a weight average molecular weight of from about 40,000 to about 2,000,000.

The compounds of Formulas (III), (IV), (V), and (VI) can generally be combined with any polymer binder. Exemplary polymer binders include the polymer binders discussed above, and other polymers such as poly(vinyl cinnamate), polysiloxanes, polypyrroles, polyacrylates, polymethacrylates, polyesters, and mixtures thereof. The polymers may have a weight average molecular weight of from about 10,000 to about 2,000,000, including from about 40,000 to about 1,000,000.

The weight ratio of the small molecule semiconductor of Formula (I) to the polymer binder may be from about 99:1 to about 1:3, including from about 10:1 to about 1:2, from about 5:1 to about 2:3, or from about 3:2 to about 3:4. In some embodiments, the weight ratio of the small molecule semiconductor of Formula (I) to the polymer binder is around 1:1. The weight ratio of the small molecule semiconductor of Formula (II) to the styrene-based polymer binder is desirably from about 3:2 to about 2:3, and works optimally at a ratio of about 1:1.

The semiconductor composition may further comprise a solvent in which the small molecule semiconductor and the polymer binder are soluble. Exemplary solvents used in the solution may include chlorinated solvents such as chlorobenzene, chlorotoluene, dichlorobenzene, dichloroethane, chloroform, trichlorobenzene, and the like; alcohols and diols such as propanol, butanol, hexanol, hexanediol, etc.; hydrocarbons or aromatic hydrocarbons such as hexane, heptane, toluene, decalin, xylene, ethyl benzene, tetrahydronaphthalene, methyl naphthalene, mesitylene, trimethyl benzene, etc.; ketones such as acetone, methyl ethyl ketone, etc.; acetates, such as ethyl acetate; pyridine, tetrahydrofuran, and the like.

The small molecule semiconductor and the polymer binder are from about 0.05 to about 20 weight percent of the semiconductor composition, including from about 0.1 to about 10 weight percent of the semiconductor composition, or from about 0.1 to about 1.0 weight percent of the semiconductor composition.

In embodiments, the semiconductor composition comprising the small molecule semiconductor and the polymer binder may have a viscosity of from about 1.5 centipoise (cps) to about 100 cps, including from about 2 to about 20 cps. The use of a high molecular weight polymer binder will increase the viscosity of the semiconductor composition. As a result, it will help to form a uniform semiconductor layer upon using solution deposition techniques such as inkjet printing and spin coating.

Bottom-gate TFTs may be advantageous because they are generally simpler to fabricate. However, previous semiconductor/polymer composite systems have only achieved high mobility in top-gate devices. When the semiconductor composition of the present disclosure is utilized, high mobility can also be achieved in both top-gate TFTs and bottom-gate devices like those shown in FIGS. 1-3.

The semiconducting layer may be formed in an electronic device using conventional processes known in the art. In embodiments, the semiconducting layer is formed using solution depositing techniques. Exemplary solution depositing techniques include spin coating, blade coating, rod coating, dip coating, screen printing, ink jet printing, stamping, stencil printing, screen printing, gravure printing, flexography printing, and the like.

After being deposited, the semiconductor composition is optionally thermally treated (for example, by drying or annealing) at an elevated temperature which is lower than the melting point of the small molecule semiconductor used in the semiconductor composition. Depending on the small molecule semiconductor used, the temperature of the thermal treatment may vary. For example, the thermal treatment may be carried out at a temperature of less than 200° C., less than 150° C., or less than 100° C. Generally, the semiconductor layer will not undergo a thermal treatment process having a temperature higher than the melting point of the small molecule semiconductor. In some embodiments, particularly those which use the small molecule semiconductor of Formula (I), there is absent of an annealing step during the fabrication of a semiconductor layer from the semiconductor composition. Annealing at a temperature higher than the melting point of the small molecule semiconductor would cause significant phase separation of the small molecule semiconductor and the polymer binder, as well as increasing the average crystal size of the small molecule semiconductor. As a result, the electronic device would show poor electrical performance. The semiconducting layer with depressed crystal size has a field effect mobility of at least 0.2 $cm^2/V \cdot sec$, or at least 0.4 $cm^2/V \cdot sec$, or at least 0.5 $cm^2/V \cdot sec$, including at least 0.7 $cm^2/V \cdot sec$.

The semiconducting layer with the depressed crystal size can be prepared with a variety of processing methods. In particular, semiconductor layers having the depressed crystallinity of the present disclosure can be made by spin-coating the semiconducting compositions onto a surface. High spin-coating speeds are correlated to reduced small molecule semiconductor crystal sizes. It is generally believed that high crystallinity and large crystal size are ideal for high charge carrier mobility. However, unexpectedly, reduced crystal size improved the mobility of the composite system of the present disclosure. Layers where the crystalline small molecule semiconductor has an average crystal size of 50 nanometers or less can be obtained by spin-coating which is performed at a spin speed of at least 2000 revolutions per minute (rpm). In particular embodiments, the semiconducting composition is deposited by spin-coating at a speed of at least 2,500 rpm, at least 3,000 rpm, at least 3,500 rpm, or at least 4,000 rpm.

One indication of depressed crystallinity is in the average crystal size of the crystalline small molecule semiconductor. In embodiments, the average crystal size of the small molecule semiconductor in the semiconducting layer of the present disclosure is 100 nanometers or less. In specific embodiments, the average crystal size is 50 nanometers or less. In more specific embodiments, the average crystal size is 35 nanometers or less. The crystalline small molecule semiconductor generally has a crystal size greater than 5 nanometers. The average crystal size can be measured using methods such as X-ray diffraction, transmission electron microscopy (TEM), scanning electron microscopy (SEM), atomic force microscopy (AFM), etc. The measurement of the average crystal size is expressed as the diameter of a spherical volume. However, this should not be construed as requiring the crystals of the small molecule semiconductor to have a particular morphology or shape.

Another indication of depressed crystallinity can be found in an X-ray diffraction pattern of the crystalline semiconductor or a semiconductor layer comprising the crystalline semiconductor and a polymer binder as described above. When the primary diffraction peak is examined, the diffraction peak has a Full Width at Half Maximum (FWHM) of 0.20 degrees 2θ or greater. In specific embodiments, the FWHM is 0.25 degrees or greater. In particular embodiments, the FWHM is less than 0.5 degrees 2θ. In other embodiments, the FWHM is from about 0.20 to about 0.35 degrees 2θ.

The semiconducting layer formed using the semiconductor composition can be from about 5 nanometers to about 1000 nanometers deep, including from about 20 to about 100 nanometers in depth. In certain configurations, such as the configurations shown in FIGS. 1 and 4, the semiconducting layer completely covers the source and drain electrodes.

The performance of a TFT can be measured by mobility. The mobility is measured in units of $cm^2/V \cdot sec$, higher mobility is desired. The resulting TFT using the semiconductor composition of the present disclosure may have a field effect mobility of at least 0.1 $cm^2/V \cdot sec$, including at least 0.4 $cm^2/V \cdot sec$. The TFT of the present disclosure may have a current on/off ratio of at least $10^5$, including at least $10^6$. The TFT comprising the semiconductor layer comprising the small molecule semiconductor of Formula (I) and a polymer binder has excellent stability in air. For example, upon exposure the ambient air, the field effect mobility may increase initially then leveled off. No decrease of field effect mobility over 2 weeks, including over 1 month.

A thin film transistor generally includes a substrate, an optional gate electrode, source electrode, drain electrode, and a dielectric layer in addition to the semiconducting layer.

The substrate may be composed of materials including but not limited to silicon, glass plate, plastic film or sheet. For structurally flexible devices, plastic substrate, such as for example polyester, polycarbonate, polyimide sheets and the like may be preferred. The thickness of the substrate may be from about 10 micrometers to over 10 millimeters with an exemplary thickness being from about 50 to about 100 micrometers, especially for a flexible plastic substrate and from about 0.5 to about 10 millimeters for a rigid substrate such as glass or silicon.

The dielectric layer generally can be an inorganic material film, an organic polymer film, or an organic-inorganic composite film. Examples of inorganic materials suitable as the dielectric layer include silicon oxide, silicon nitride, aluminum oxide, barium titanate, barium zirconium titanate and the like. Examples of suitable organic polymers include polyesters, polycarbonates, poly(vinyl phenol), polyimides, polystyrene, polymethacrylates, polyacrylates, epoxy resin and the like. The thickness of the dielectric layer depends on the dielectric constant of the material used and can be, for example, from about 10 nanometers to about 500 nanometers. The dielectric layer may have a conductivity that is, for example, less than about $10^{-12}$ Siemens per centimeter (S/cm). The dielectric layer is formed using conventional processes known in the art, including those processes described in forming the gate electrode.

In the present disclosure, the dielectric layer may be surface modified with a surface modifier. The semiconducting layer can be directly contacted with this modified dielectric layer surface. The contact may be complete or partial. This surface modification can also be considered as forming an interfacial layer between the dielectric layer and the semiconducting layer. In particular embodiments, the surface of the dielectric layer has been modified with an organosilane agent of Formula (A):

(L)$_t$-[SiR$_m$(R')$_{4-m-t}$]$_v$  Formula (A)

wherein R is alkyl, R' is halogen or alkoxy; m is an integer from 1 to 4; L is a linking atom; t is 0 or 1, and indicates whether a linking atom is present; and v indicates the number of trisubstituted silyl groups on the linking atom. The sum of (m+t) is never greater than 4. When t is 0, v is automatically 1. Exemplary organosilane agents of Formula (A) include hexamethyldisilazane (HMDS) (L=NH, t=1, R=methyl, m=3, v=2) and octyltrichlorosilane (OTS-8) (t=0, R=octyl, m=1, R'=chloro, v=1).

The gate electrode is composed of an electrically conductive material. It can be a thin metal film, a conducting polymer film, a conducting film made from conducting ink or paste, or the substrate itself, for example heavily doped silicon. Examples of gate electrode materials include but are not restricted to aluminum, gold, silver, chromium, indium tin oxide, conductive polymers such as polystyrene sulfonate-doped poly(3,4-ethylenedioxythiophene) (PSS-PEDOT), and conducting ink/paste comprised of carbon black/graphite. The gate electrode can be prepared by vacuum evaporation, sputtering of metals or conductive metal oxides, conventional lithography and etching, chemical vapor deposition, spin coating, casting or printing, or other deposition processes. The thickness of the gate electrode ranges for example from about 10 to about 200 nanometers for metal films and from about 1 to about 10 micrometers for conductive polymers. Typical materials suitable for use as source and drain electrodes include those of the gate electrode materials such as aluminum, gold, silver, chromium, zinc, indium, conductive metal oxides such as zinc-gallium oxide, indium tin oxide, indium-antimony oxide, conducting polymers and conducting inks. Typical thicknesses of source and drain electrodes are, for example, from about 40 nanometers to about 1 micrometer, including more specific thicknesses of from about 100 to about 400 nanometers.

Typical materials suitable for use as source and drain electrodes include those of the gate electrode materials such as gold, silver, nickel, aluminum, platinum, conducting polymers, and conducting inks. In specific embodiments, the electrode materials provide low contact resistance to the semiconductor. Typical thicknesses are about, for example, from about 40 nanometers to about 1 micrometer with a more specific thickness being about 100 to about 400 nanometers. The OTFT devices of the present disclosure contain a semiconductor channel. The semiconductor channel width may be, for example, from about 5 micrometers to about 5 millimeters with a specific channel width being about 100 micrometers to about 1 millimeter. The semiconductor channel length may be, for example, from about 1 micrometer to about 1 millimeter with a more specific channel length being from about 5 micrometers to about 100 micrometers.

The source electrode is grounded and a bias voltage of, for example, about 0 volt to about 80 volts is applied to the drain electrode to collect the charge carriers transported across the semiconductor channel when a voltage of, for example, about +10 volts to about −80 volts is applied to the gate electrode. The electrodes may be formed or deposited using conventional processes known in the art.

If desired, a barrier layer may also be deposited on top of the TFT to protect it from environmental conditions, such as light, oxygen and moisture, etc. which can degrade its electrical properties. Such barrier layers are known in the art and may simply consist of polymers.

The various components of the OTFT may be deposited upon the substrate in any order. Generally, however, the gate electrode and the semiconducting layer should both be in contact with the gate dielectric layer. In addition, the source and drain electrodes should both be in contact with the semiconducting layer. The phrase "in any order" includes sequential and simultaneous formation. For example, the source electrode and the drain electrode can be formed simultaneously or sequentially. The term "on" or "upon" the substrate refers to the various layers and components with reference to the substrate as being the bottom or support for the layers and components which are on top of it. In other words, all of the components are on the substrate, even though they do not all directly contact the substrate. For example, both the dielectric layer and the semiconductor layer are on the substrate, even though one layer is closer to the substrate than the other layer. The resulting TFT has good mobility and good current on/off ratio.

The following examples are for purposes of further illustrating the present disclosure. The examples are merely illustrative and are not intended to limit devices made in accordance with the disclosure to the materials, conditions, or process parameters set forth therein. All parts are percentages by volume unless otherwise indicated.

EXAMPLES

Synthesis of Small Molecule Semiconductor 2,7-ditridecyl-[1]benzothieno[3,2-b]benzothiophene (2,7-ditridecyl-BTBT) (Formula (49)) was produced as follows.

A 50 mL Schlenk flask was charged with 2,7-diiodo-BTBT (0.51 grams, 1.036 mmol) and tridec-1-yne (0.934 grams, 5.18 mmol). Toluene (15 ml) and diisopropylamine (15 ml) were added and the reaction was degassed with two freeze/pump/thaw cycles. To the frozen reaction mixture was added bis(triphenylphosphine)palladium(II) chloride (0.145 grams, 0.207 mmol) and copper(I) iodide (0.079 grams, 0.415 mmol). The reaction was subjected to a final freeze/pump/thaw cycle and stirred under argon. After 18 hours the reaction was filtered and the filtrate was concentrated to dryness using a rotary evaporator. The crude product was purified using a Biotage SP1 chromatography system (50 grams SNAP, 0-20% CH$_2$Cl$_2$ in hexanes). The product, 2,7-ditridecyn-1-yl-BTBT, was isolated and recrystallized from hexanes. The structure was confirmed by $^1$H and $^{13}$C NMR spectroscopy. A yield of 0.25 g (40%) was realized. This step is illustrated below:

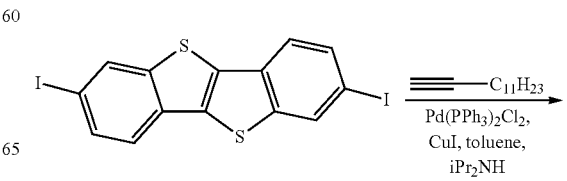

-continued

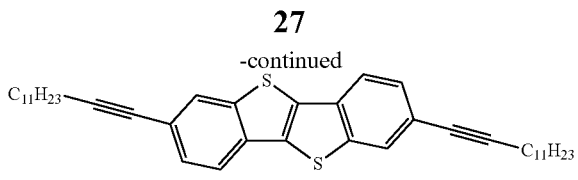

Next, in a 250 mL round-bottomed flask a solution of 2,7-ditridecyn-1-yl-BTBT (0.47 grams, 0.787 mmol) in tetrahydrofuran (50 ml) was treated with Pd/C (0.5 grams, 4.70 mmol). The flask was carefully evacuated under vacuum and purged with $H_2$ gas three times. The reaction was stirred under an $H_2$ atmosphere (balloon) until no starting material was detected by TLC. After 18 hours the reaction was concentrated on a rotary evaporator, resuspended in hexane and filtered through a short silica plug (hexanes). The product was practically pure by TLC and was recrystallized from hexanes. The structure was confirmed by $^1$H and $^{13}$C NMR spectroscopy. A yield of 0.40 g (84%) was realized to obtain the final product. This step is illustrated below:

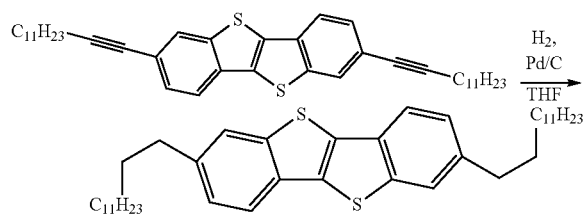

Synthesis of Small Molecule Semiconductor 2,7-dipentyl-[1]benzothieno[3,2-b]benzothiophene was produced (2,7-dipentyl-BTBT) (Formula (46)).

In a 250 mL 3-neck round-bottomed flask benzo[b]benzo[4,5]thieno[2,3-d]thiophene (1 grams, 4.16 mmol) was dissolved in $CH_2Cl_2$ (100 ml) and cooled to minus 10° C. The reaction was treated with $AlCl_3$ (3.05 grams, 22.88 mmol) and the resulting brown suspension was cooled to −78° C. The reaction was treated dropwise with pentanoyl chloride (2.52 ml, 20.80 mmol) and the resulting red suspension was stirred at this temperature under an Argon atmosphere. After 1 hour, the cooling bath was removed and the reaction was warmed to room temperature and stirred under an Argon atmosphere. After 48 hours the reaction was poured over ice and was stirred for 1 hour. The crude product was collected by vacuum filtration and washed sequentially with water (50 mL) and methanol (50 mL). The crude product was purified by recrystallization from toluene. The structure was confirmed by $^1$H and $^{13}$C NMR spectroscopy. A yield of 0.65 g (38%) was realized.

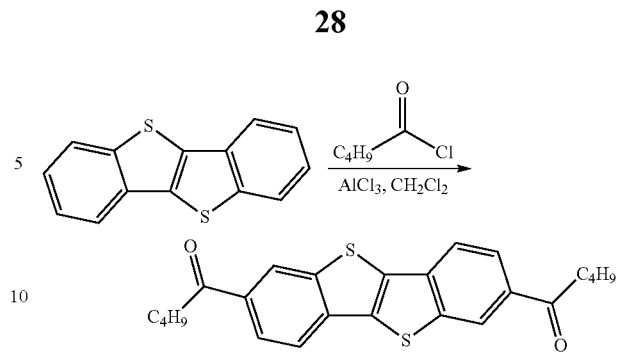

In a 250 mL 3-necked round-bottomed flask potassium hydroxide (0.453 g, 8.08 mmol) was dissolved in diethylene glycol (70 ml). The reaction was treated with 1,1'-(benzo[b]benzo[4,5]thieno[2,3-d]thiophene-2,7-diyl)bis(pentan-1-one) (0.600 g, 1.469 mmol) and hydrazine monohydrate (1.817 ml, 37.4 mmol) and the resulting suspension was heated to 100° C. After 1 hour the reaction was heated to 210° C. After 5 hours the heating source was removed and the reaction was cooled to room temperature and stirred overnight. The crude product was collected by vacuum filtration, then washed with water (50 mL) and methanol (50 mL). The product was purified by column chromatography on silica gel eluting with hexane and then recrystallized from hexane. The structure was confirmed by $^1$H and $^{13}$C NMR spectroscopy. A yield of 0.25 g (45%) was realized to obtain the final product.

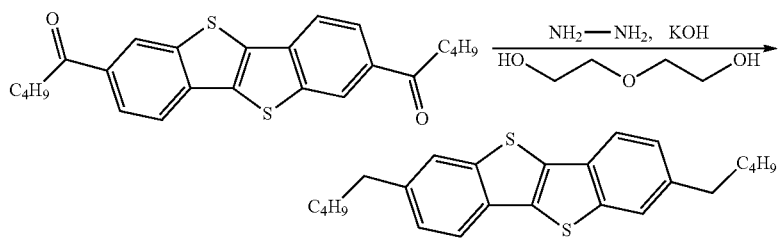

Examples 1-3

Devices comprising a semiconducting layer formed from a semiconductor composition comprising 2,7-ditridecyl-BTBT and polystyrene having a weight average molecular weight of about 280,000 were fabricated. An n-doped silicon wafer was used as the substrate. A 200 nm thick silicon oxide dielectric layer was thermally grown as a layer on the substrate. 2,7-ditridecyl-BTBT and polystyrene at a 1:1 weight ratio were dissolved in chlorobenzene in a total amount of 0.7 wt % of the resulting solution. The solution was filtered with a 1.0 μm syringe and spin coated onto the substrate at different spin speeds.

In Example 1, the solution was spin coated onto the substrate at a spin speed of 1,000 rpm.

In Example 2, the solution was spin coated onto the substrate at a spin speed of 2,000 rpm.

In Example 3, the solution was spin coated onto the substrate at a spin speed of 4,000 rpm.

Multiple devices were made under the conditions of each Example. After drying at 70 to 80° C. for 30 minutes, gold source and drain electrodes were vacuum evaporated on top of the semiconductor layer to complete the devices. The semiconducting layers were not annealed. The transistor devices were characterized with a KEITHLEY® 4200 Semiconductor Characterization System at ambient conditions.

Table 1 summarizes the performance of the transistors having the semiconductor layer prepared with different spin speeds:

TABLE 1

Spin Speed and Mobility of Examples 1-3

| Example | Spin Speed (rpm) | Average Mobility (cm$^2$/V – s) | High Mobility (cm$^2$/V – s) |
|---|---|---|---|
| 1 | 1000 | 0.02 | 0.1 |
| 2 | 2000 | 0.1 | 0.4 |
| 3 | 4000 | 0.48 | 0.87 |

Figure 5A:
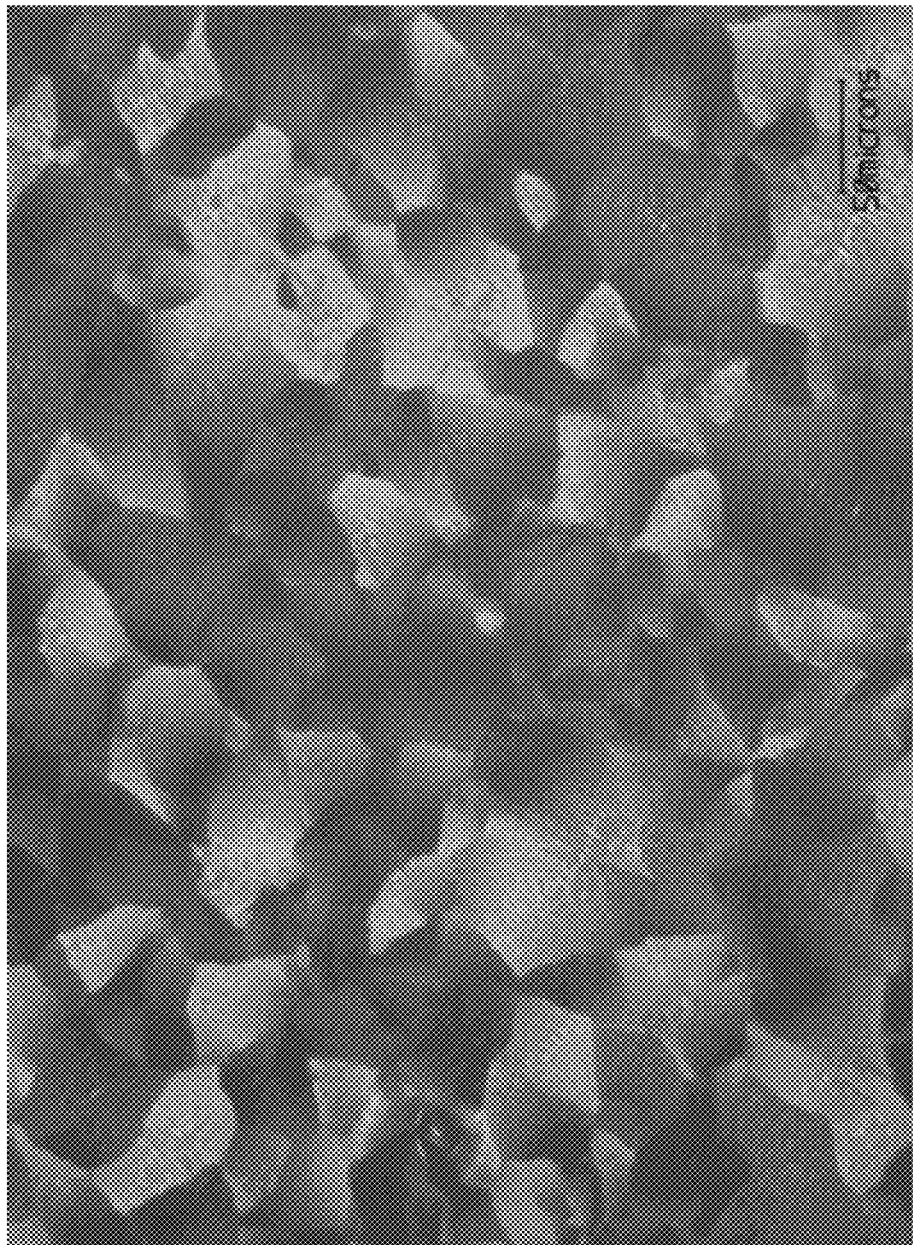
FIG. 5A is a polarized microscopic image of a semiconductor layer of the present disclosure which was deposited by spin coating at a speed of about 1,000 revolutions per minute (RPMs).
Figure 5B:
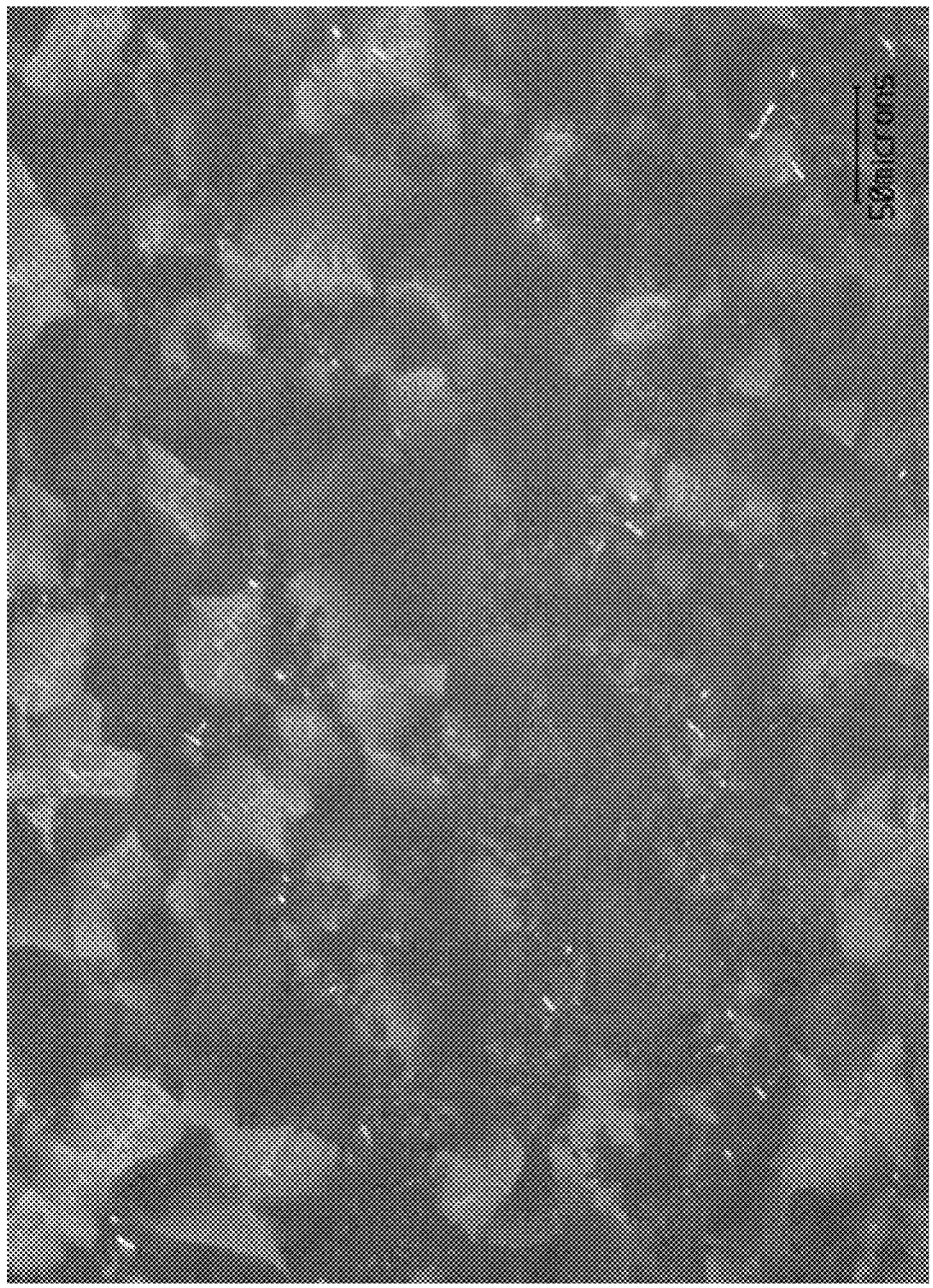
FIG. 5B is a polarized microscopic image of a semiconductor layer of the present disclosure which was deposited by spin coating at a speed of about 2,000 RPMs.
Figure 5C:
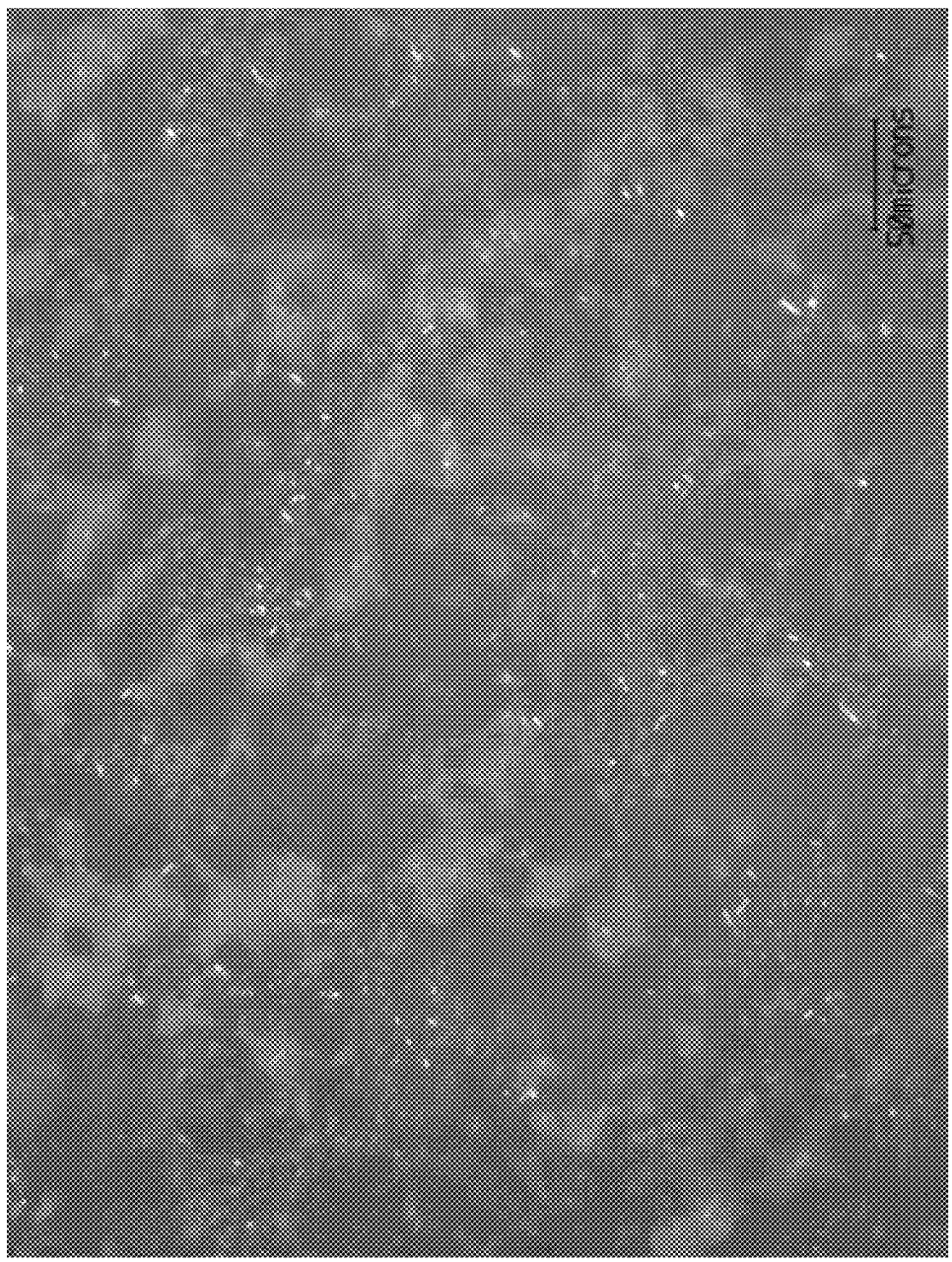
FIG. 5C is a polarized microscopic image of a semiconductor layer of the present disclosure which was deposited by spin coating at a speed of about 4,000 RPMs.

As seen in Examples 1-3, mobility (both average and high value) increased with increasing spin speed. The morphology of a semiconducting layer spin-coated at 1000 rpm is shown in FIG. 5A. Large, well-defined crystals were observed and the crystals had a crystal size of more than 50 μm. FIG. 5B shows the morphology of a semiconducting layer spin coated at 2000 rpm. The crystal size is noticeably reduced. In FIG. 5C, significantly depressed crystallinity was observed at the higher speed.

Examples 4-8

Several batches of devices were fabricated and X-ray diffraction studies were conducted to obtain more quantitative results. In each case, the semiconducting layer was spin coated at a speed of 4000 rpm.

In Examples 4-6, the small molecule semiconductor was 2,7-ditridecyl-BTBT and the semiconducting layer was not annealed.

In Example 7, the small molecule semiconductor was 2,7-ditridecyl-BTBT and the semiconducting layer was annealed at 130 degrees C. for 10 minutes.

In Example 8, the small molecule semiconductor was BTBT and the semiconducting layer was not annealed.

Table 2 summarizes the performance of transistors of Examples 4-8:

TABLE 2

Mobility of Examples 4-8

| Example | Semiconductor | Annealed? | Average Mobility (cm$^2$/V – s) | Highest Mobility (cm$^2$/V – s) |
|---|---|---|---|---|
| 4 | 2,7-ditridecyl-BTBT | No | 0.5 | 0.77 |
| 5 | 2,7-ditridecyl-BTBT | No | 0.48 | 0.87 |
| 6 | 2,7-ditridecyl-BTBT | No | 0.440 | 0.72 |
| 7 | 2,7-ditridecyl-BTBT | Yes | 0.003 | 0.02 |
| 8 | BTBT | No | No Mobility | — |

Figure 6:
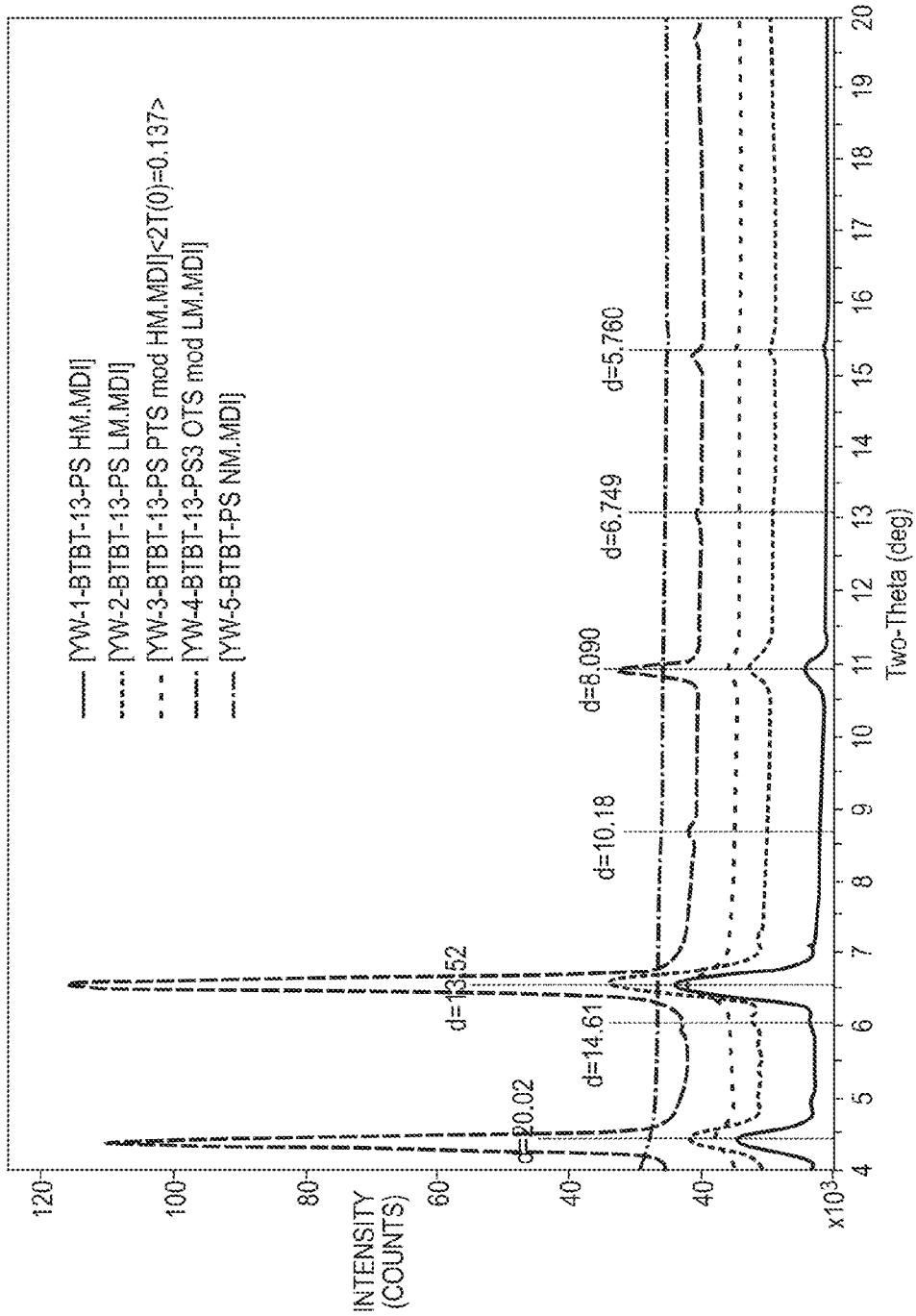
FIG. 6 is a graph showing the x-ray diffraction patterns of different semiconductor films of the present disclosure.

The X-ray diffraction patterns of Examples 4-8 are shown in FIG. 6. The blue, red, and black curves show the X-ray diffraction patterns of Examples 4-6 respectively. The green curve shows the X-ray diffraction pattern of Example 7. The peach curve shows the X-ray diffraction pattern of Example 8.

The BTBT/PS blend (Example 8) exhibited an amorphous nature and no mobility was detected in the device. The device with the annealed semiconducting layer (Example 7) showed very sharp diffraction peaks and exhibited very low mobility. The devices with the 2,7-ditridecyl-BTBT/PS blend which was not annealed exhibited low crystallinity and high mobility.

The average Full Width at Half Maximum (FWHM) for each of Examples 4-7 was determined from the X-ray diffraction patterns. The primary diffraction peak was located at approximately 4.4° (2θ). Table 3 shows the FWHMs and crystal sizes:

TABLE 3

FWHM and Crystal Size

| Example | Average FWHM (deg 2Θ) | Crystallite Size (nm) |
|---|---|---|
| 4 | 0.294 | 33.7 |
| 5 | 0.295 | 33.9 |
| 6 | 0.319 | 30.8 |
| 7 | 0.143 | >100 |

Examples 4-6, the high mobility examples, show an average FWHM two times larger than the FWHM of Example 7. The crystal size in the high mobility examples was less than 35 nm. In fact, the three batches of high performance semiconducting layers showed good reproducibility around about 31 to about 34 nm. On the other hand, the low mobility sample showed a much larger crystal size of over 100 nm. The diffraction peak at d-spacing of 10.18 angstroms (Å) was also missing in the high mobility films.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

The invention claimed is:

1. An electronic device comprising a semiconducting layer, the semiconducting layer comprising:
    an amorphous polymer binder; and
    a crystalline small molecule semiconductor having an average crystal size which is at least two times smaller than that of the small molecule semiconductor in a semiconducting layer that has been thermally treated at a temperature greater than the melting temperature of the small molecule semiconductor;
    wherein the semiconducting layer has a field-effect mobility of at least 0.2 cm$^2$/V·sec, and
    wherein the crystalline small molecule semiconductor has the structure of Formula (II):

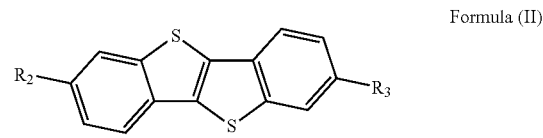

Formula (II)

wherein R2 and R3 are independently selected from alkenyl, substituted alkenyl, alkenyl, substituted alkenyl, aryl, substituted aryl, heteroaryl, substituted heteroaryl, alkoxy, alkylthio, trialkylsilyl, ketonyl, cyano, and halogen.

2. The electronic device of claim 1, wherein the small molecule semiconductor has an average crystal size of 100 nanometers or less.

3. The electronic device of claim 1, wherein the polymer binder is a styrene-based polymer or an arylamine-based polymer.

4. The electronic device of claim 1, wherein the polymer binder is polystyrene, poly(α-methyl styrene), poly(4-methyl styrene), poly(alpha-methyl styrene-co-vinyl toluene), polystyrene-block-butadiene-block-styrene), poly(styrene-block-isopene-block-styrene), poly(vinyl toluene), a terpene resin, poly(styrene-co-2,4-dimethylstyrene), poly(chlorostyrene), poly(styrene-co-α-methyl styrene), poly(styrene-co-butadiene), polycarbazole, a polytriarylamine, or poly(N-vinylcarbazole).

5. The electronic device of claim 1, wherein the polymer binder is a styrene-based polymer having a weight average molecular weight of from about 40,000 to about 2,000,000.

6. The electronic device of claim 1, wherein the small molecule semiconductor has the structure of Formula (III):

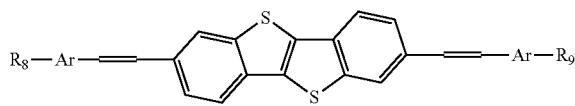

Formula (III)

wherein $R_8$, and $R_9$ are independently alkyl or substituted alkyl; and each Ar is independently an arylene or heteroarylene group.

7. An electronic device comprising a semiconducting layer, the semiconducting layer comprising:
an amorphous polymer binder; and
a crystalline small molecule semiconductor;
wherein an x-ray diffraction pattern of the semiconducting layer has a primary diffraction peak with a Full Width at Half Maximum (FWHM) that is at least two times greater than a FWHM of a semiconducting layer comprising the small molecule semiconductor that has been thermally treated at a temperature greater than the melting temperature of the small molecule semiconductor,
wherein the semiconducting layer has a field-effect mobility of at least 0.2 cm²/V·sec, and
wherein the small molecule semiconductor has the structure of Formula (II):

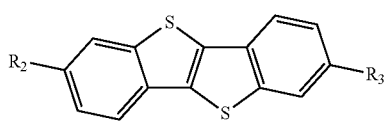

Formula (II)

wherein R2 and R3 are independently selected from alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen.

8. The electronic device of claim 7, wherein the x-ray diffraction pattern of the semiconductor layer has a primary diffraction peak with a FWHM of 0.20 degrees 2Θ or greater.

9. The electronic device of claim 7, wherein the small molecule semiconductor has an average crystal size of 100 nanometers or less.

10. The electronic device of claim 7, wherein the polymer binder is a styrene-based polymer or an arylamine-based polymer.

11. The electronic device of claim 7, wherein the polymer binder is polystyrene, poly(α-methyl styrene), poly(4-methyl styrene), poly(alpha-methyl styrene-co-vinyl toluene), poly(styrene-block-butadiene-block-styrene), poly(styrene-block-isopene-block-styrene), polyvinyl toluene), a terpene resin, poly(styrene-co-2,4-dimethylstyrene), poly(chlorostyrene), poly(styrene-co-α-methyl styrene), poly(styrene-co-butadiene), polycarbazole, a polytriarylamine, or poly(N-vinylcarbazole).

12. The electronic device of claim 7, wherein the polymer binder is a styrene-based polymer having a weight average molecular weight of from about 40,000 to about 2,000,000.

13. An electronic device comprising a semiconducting layer, the semiconducting layer comprising:
an amorphous polymer binder; and
a small molecule semiconductor having the structure of Formula (II):

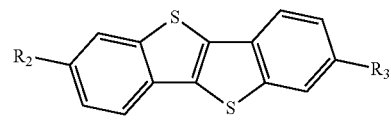

Formula (II)

wherein R2 and R3 are independently selected from alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen,
wherein the small molecule semiconductor has an average crystal size of 100 nanometers or less in the semiconductor layer.

14. The electronic device of claim 13, wherein the polymer binder is a styrene-based polymer or an arylamine-based polymer.

15. The electronic device of claim 14,
wherein the small molecule semiconductor has an average crystal size of 50 nm or less in the semiconductor layer.

16. The electronic device of claim 14, wherein the polymer binder is polystyrene, poly(α-methyl styrene), poly(4-methyl styrene), poly(alpha-methyl styrene-co-vinyl toluene), poly(styrene-block-butadiene-block-styrene), poly(styrene-block-isopene-block-styrene), poly(vinyl toluene), a terpene resin, poly(styrene-co-2,4-dimethylstyrene), poly(chlorostyrene), poly(styrene-co-α-methyl styrene), poly(styrene-co-butadiene), polycarbazole, a polytriarylamine, or poly(N-vinylcarbazole).

17. The electronic device of claim 14, wherein the polymer binder is a styrene-based polymer having a weight average molecular weight of from about 40,000 to about 2,000,000.

* * * * *